United States Patent [19]
Heinz et al.

[11] Patent Number: 5,880,138
[45] Date of Patent: Mar. 9, 1999

[54] NMDA RECEPTOR SELECTIVE ANTAGONISTS

[75] Inventors: Lawrence J. Heinz, Pittsboro; William H. W. Lunn, Indianapolis; Paul L. Ornstein, Carmel, all of Ind.

[73] Assignee: Eli Lilly and Company, Indianapolis, Ind.

[21] Appl. No.: 953,951

[22] Filed: Oct. 20, 1997

Related U.S. Application Data

[60] Provisional application No. 60/027,731 Oct. 1, 1996.
[51] Int. Cl.$^6$ ................... A61K 31/005; C07D 401/12
[52] U.S. Cl. ............................. 514/326; 546/210
[58] Field of Search .................. 514/326; 546/210

[56] References Cited

U.S. PATENT DOCUMENTS

| | | | |
|---|---|---|---|
| 4,902,687 | 2/1990 | Ornstein | 514/253 |
| 4,968,678 | 11/1990 | Ornstein | 514/222.2 |
| 5,192,751 | 3/1993 | Thor | 514/82 |
| 5,331,001 | 7/1994 | Hamilton | 514/381 |

FOREIGN PATENT DOCUMENTS

| | | |
|---|---|---|
| 330 353 | 8/1989 | European Pat. Off. . |
| 488 959 | 6/1992 | European Pat. Off. . |

OTHER PUBLICATIONS

Ornstein, et al., *J. Med. Chem.* (1991), 34, pp. 90–97.
Ornstein, et al., *J. Med. Chem.* (1992), 35, pp. 3111–3115.
Ornstein, et al., *J. Med. Chem.* (1992), 35, pp. 3547–3560.
Yoshiyama, et al., *Br. J. Pharmacol.* (1993), 110, pp. 77–86.
Schoepp, et al., *Eur. J. Pharmacol.* (1990), 182(3), pp. 421–427.

*Primary Examiner*—Ceila Chang
*Attorney, Agent, or Firm*—Nelsen L. Lentz

[57] ABSTRACT

This invention discloses novel piperidine tetrazole compounds which are selective antagonists of EAA receptors particularly the NMDA receptors. The invention also provides formulations of the preferred compounds and for methods of using the compounds to treat various disorders associated with neuronal excitotoxicity.

12 Claims, No Drawings

NMDA RECEPTOR SELECTIVE ANTAGONISTS

This application claims the benefit of U.S. Provisional Application No. 60/027,731 filed Oct. 1, 1996.

FIELD OF THE INVENTION

This invention relates to compounds which are antagonists of the excitatory amino acid receptors of the mammalian central nervous system, and will have special application to those compounds which selectively antagonize the NMDA receptors.

BACKGROUND OF THE INVENTION

In the mammalian central nervous system (CNS), the transmission of nerve impulses is controlled by the interaction action between a neurotransmitter and a surface receptor. Neurotransmitters, such as L-glutamate and L-aspartate, are released by the sending neurons and travel across the synapse where they interact with the surface receptor of the receiving neuron. Such neurotransmitters are referred to as excitatory amino acids (EAA's) because they mediate the major excitatory pathways in the CNS. Likewise, the surface receptors that respond to EAA's are generally referred to as EAA receptors.

EAA receptors are of two principle classes; the "lionotropic" receptors which are directly coupled to the cell membrane adjacent to the cation channel openings; and the "metabotropic" receptors which are G-proteins coupled to multiple second messenger systems which produce enhanced phosphoinositide (PI) hydrolysis, activation of phospholipase D, changes in cAMP formation and changes in ion channel function.

Ionotropic receptors are subclassed into at least three major groups, based upon their sensitivity to a selective agonist. The three major groups are generally referred to as the N-methyl-D aspartate (NMDA) group; the α-amino-3-hydroxy-5-methyl-isoxazole-4 propionic acid (AMPA) group; and the kainic acid (KA) group.

EAA's and their receptors play an important role in a variety of physiological processes, such as long-term potentiation (LTP), synaptic plasticity, motor control, respiration, cardiovascular regulation and sensory perception.

Excessive or inappropriate stimulation of EAA receptors generally leads to neuronal cell damage or cell death by excitotoxicity. Excitotoxicity has been suggested as the major cause of neuronal degeneration in a number of CNS diseases and conditions, such as Alzheimer's Disease, Huntington's Chorea, amyotrophic lateral sclerosis (ALS), cerebral ischemia and many other related neurodegenerative diseases.

It has been suggested that the blocking actions of antagonist compounds can abate the cell death caused by excitotoxicity. Selective antagonists which block the action of certain types or subtypes of EAA receptors have been synthesized and tested in the part, particularly at the NMDA receptors. Prior examples of NMDA selective antagonists are described and claimed in U.S. Pat. No. 4,968,678 issued Nov. 6, 1990 and U.S. Pat. No. 5,284,957, issued Feb. 8, 1994. Selective antagonists could be particularly useful in individuals who demonstrate receptor selective excitotoxicity.

SUMMARY OF THE INVENTION

The present invention provides compounds which are selective antagonists of NMDA receptors. More specifically the invention provides for compounds of the formula:

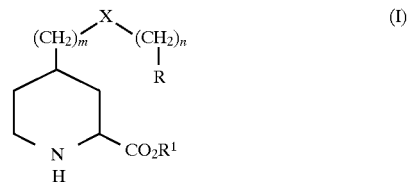

wherein:
X is =NO—, —O—, 'S— or —(CH$_2$)$_q$—;
m, n and q are 0 or 1;
R is

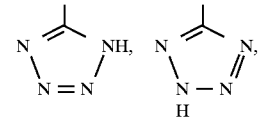

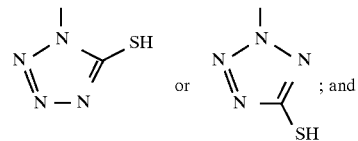

$R^1$ is H or a carboxyl protecting group;
or a pharmaceutically acceptable salt, racemate or isomer thereof, provided that;
when X is —O—, n must be 1;
when X is —O—, —S— or =NO—, R must be

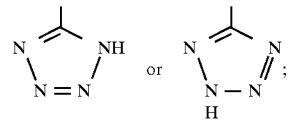

when X is =NO—, m must be 0;
and when X is (CH$_2$)$_q$, R must be

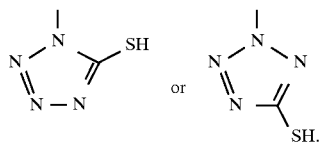

The invention also provides for pharmaceutical formulations which include a compound according to Formula I and a pharmaceutically acceptable carrier, excipient or diluent therefor.

The invention also provides for a method of blocking one or more EAA receptors, particularly the NMDA receptor, and to methods for treating various disorders which have been linked to the EAA receptors. Such disorders may include, but not being limited to, acute neurological disorders such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The formula I compounds are believed to have the ability to treat a variety of chronic neurological disorders, such as Alzheimer's disease, Huntington's Chorea, amytrophic lateral sclerosis, AIDS-induced dementia, ocular damage and retinopathy, cognitive disorders, and idiopathic and drug-induced Parkinson's. The present invention also provides methods for treating these disorders which comprises administering to a patient in need thereof an effective amount of a compound of formula I or a pharmaceutically acceptable racemate or isomer thereof, or a pharmaceutically acceptable salt thereof.

The formula I compounds of the present invention are also believed to have the ability to treat a variety of other neurological disorders in mammals that are associated with glutamate dysfunction, including muscular spasms, convulsions, migraine headaches, urinary incontinence, nicotine withdrawal, psychosis, (such as schizophrenia) opiate tolerance and withdrawal, anxiety, emesis, brain edema, chronic pain, and tardive dyskinesia. The formula I compounds are also useful as antidepressant and analgesic agents. Therefore, the present invention also provides methods for treating these disorders which comprise administering to a patient in need thereof an effective amount of the compound of formula I, or a pharmaceutically acceptable racemate or isomer or a pharmaceutically acceptable salt thereof.

DESCRIPTION OF THE PREFERRED EMBODIMENTS

The terms and abbreviations used in the instant examples have their normal meanings unless otherwise designated. For example, "°C." refers to degrees Celsius; "N" refers to normal or normality; "mmol" refers to millimole or millimoles; "g" refers to gram or grams; "ml" means milliliter or milliliters; "M" refers to molar or molarity.

The compounds of the present invention possess two asymmetric carbon atoms represented by the carbon atom of the piperidine ring which attaches to the tetrazole ring either directly or through one or more methylene groups or heteroatoms, and the carbon atom of the piperidine ring which attaches the carboxylic acid to the piperidine ring. As such, the compounds can exist as four diastereoisomers and as cis or trans isomers, each of which can exist as the racemic mixture of such isomers or each individual optical isomer. In general, the cis isomers are preferred. When a =NO— is present, it creates a third point of asymmetry, and the compounds accordingly include the individual geometric E and Z isomers and the corresponding mixtures thereof. In general, the Z isomers are preferred.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in *Nomenclature of Organic Compounds: Principles and Practice*, (J. H. Fletcher, et al., eds., 1974) at pages 103–120.

When a compound of the invention is named without a stereochemical indication, the racemate and also the diastereomers and the stereospecific isomers are intended to be included. When a specific isomer or diastereomer is intended, it will be specifically named.

While all the compounds of the formula I are useful as EEA receptor blockers, certain classes are preferred. Preferred classes of compounds of the present invention are those compounds of formula I in which:

(a) X is =NO—, —O— or —S—;
(b) X is =NO—;
(c) X is —O—;
(d) X is —S—;
(e) m is 0 or 1;
(f) n is 0 or 1;
(g) p is 0 or 1;
(h) q is 0 or 1;
(i) R is

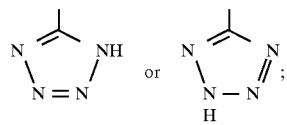

(j) R is

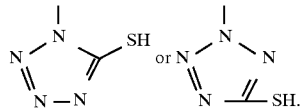

It will be understood that the above classes may be combined to form additional preferred classes.

As mentioned above, the present invention may include the pharmaceutical salts of the isomers or racemates of the Formula I compounds.

These salts can exist in conjunction with the acidic or basic portion of the molecule and can exist as acid addition, primary, secondary, tertiary or quaternary ammonium or alkali metal or alkaline earth metal salts. Acids commonly employed to form such salts include inorganic acids such as hydrochloric, hydrobromic, hydroiodic, sulfuric and phosphoric acid, as well as organic acids such as paratoluenesulfonic, methanesulfonic, oxalic, paragromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, metaphosphate, pyrophosphate, chloride, lithium, bromide, iodide, acetate, magnesium, propionate, tetramethylammonium, decanoate, caprylate, acrylate, formate, isobutyrate, caprate, heptanoate, potassium, proiolate, oxalate, trimethylammonium, malonate, succinate, suberate, sebacate, fumarate, maleate, butyne-1,4-dioate, sodium, hexyne-1,6-dioate, benzoate, chlorobenzoate, methylbenzoate, dinitrobenzoate, hydroxybenzoate, methoxybenzoate, phthalate, sulfonate, methylammonium, xylenesulfonate, phenylacetate, phenylpropionate, phenylbutyrate, citrate, lactate, calcium, β-hydroxybutyrate, gylcollate, tartrate, methanesulfonate, propanesulfonate, naphthalene-1-sulfonate, naphthalene-2-sulfonate, mandelate and the like salts.

The term "protecting group" is used herein as it is frequently used in synthetic organic chemistry, to refer to a group which will prevent a functional group from participating in a reaction carried out on some other functional group of the molecule, but which can be removed when it is desired to do so. Such groups are discussed by T. W. Greene in chapter 5 and 7 of *Protective Groups in Organic Synthesis*, John Wiley and Sons, New York, 1981, and by J. W. Barton in chapter 2 of *Protective Groups in Organic Chemistry*, J. F. W. McOmie, e., Plenum Press, New York, 1973, which are incorporated herein by reference in their entirety.

Amino protecting groups refer to a group which will prevent an amino group from participating in a reaction. Examples of amino protecting groups include benzyl and substituted benzyl such as 3,4-dimethyoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dischlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. A preferred amino-protecting group is methyl carbonate.

Carboxyl protecting groups refer to a group which will prevent a carboxyl group from participating in a reaction. Examples of carboxyl protecting group includes esters and substituted esters such as methyl, methoxy methyl, methyl thiomethyl, tetrahydropyranyl, methoxyethoxymethyl, benzloxymethyl, phenaryl, ethyl, 2,2,2-trichloroethyl, 2-methylthioethyl t-butyl, cyclopentyl, triphenylmethyl, p-bromobenzyl and trimethylsilyl. A preferred acid-protecting group is t-butyl carbonate.

It will be understood that salts of the individual stereospecific isomers or the diastereomers may be formed just as salts of the racemic mixtures are prepared.

In the most preferred compounds of this invention, R is an unsubstituted tetrazole ring. As is known in the art, tetrazole exists in two tautomeric structures, the first having the double bond at N1 and the proton on the N2 atom, referred to as a 2H-tetrazole. The second tautomer has the proton at N1 and the double bond at N4 and is called a 1-H tetrazole. Since tetrazole tautomers are in constant equilibrium, the tetrazole structures in this invention are often referred to as 1(2)H-tetrazole and they may exist individually or as a combination of the two tautomers.

Schemes I–V illustrate the general processes for synthesizing the novel compounds of this invention.

Schemes I(a), I(b) and I(c) illustrate generally the synthesis of compounds which include a sulfur heteroatom bridging the two heterocycles. The following scheme illustrates compounds where m and n are zero.

SCHEME I(a)

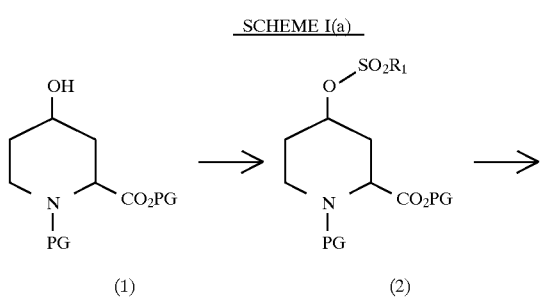

-continued
SCHEME I(a)

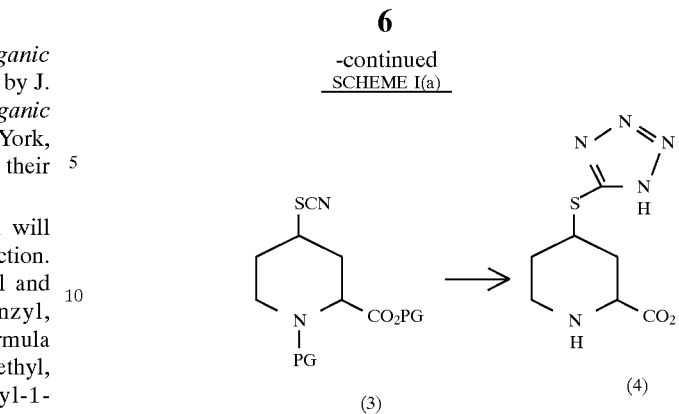

PG is a protecting group.
R₁ is methyl, phenyl, p-tolyl, p-bromophenyl, p-nitrophenyl.

As shown in Scheme I(a) (and also Schemes II and III), the preferred starting material is an N-protected-4-hydroxypiperidine-2-carboxylate. The starting material can be prepared as described by Ornstein, et al., in J. Med. Chem. (1991), 34, 90–97. The skilled artisan will appreciate that the stereochemistry of the final product may be determined by the stereo configuration of the starting material selected. If, for example, the cis isomer is selected it can readily be inverted to form the trans alcohol via a Mitsunobu reaction using trifluroacetic acid followed by hydrolysis.

The hydroxy group of the starting material is first activated for displacement using an excess of a sulfonyl halide such as methane-, phenyl-p-toluene-, p-bromophenyl-, p-nitrophenyl- or 2,4-dinitrophenylsulfonyl chloride to form the sulfonyloxy intermediate (2). The reaction can be conducted in a polar organic solvent such as pyridine or dichloromethane in the presence of 4-(N,N-dimethylamino) pyridine at a temperature ranging from –20° to 25° C., and is substantially complete in one hour to 4 days.

In a displacement reaction, intermediate (2) is reacted with an excess of thiocyanate salt to form the thiocyanate intermediate (3). An aprotic polar solvent, such as dimethylformamide, may be used and the reaction is run at temperatures from about 25° C. to about 78° C. for about one to 24 hours.

The cyano group can then be converted to the desired tetrazole by heating the thiocyanate intermediate (3) with an approximately equimolar quantity of the appropriate tetrazole forming reagent, such as azido tri-n-butylstannane, at about 72° C. to 110° C. for about 8 to 120 hours. The protecting groups may then be removed by hydrolysis with, for example, an acid such as hydrochloric acid to form the desired product (4).

Compounds where m=1 and n=0 can be prepared as follows:

Scheme I(b)

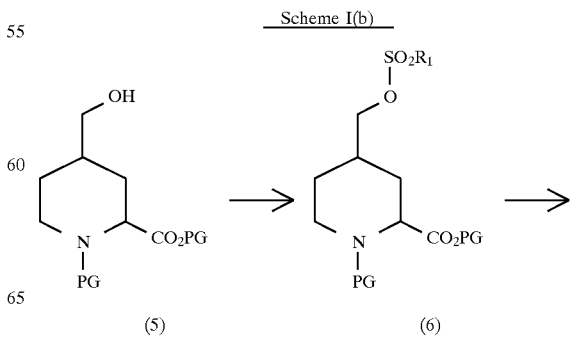

Scheme I(b)

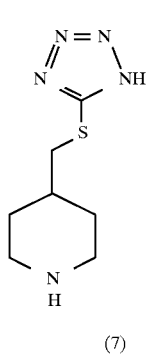

(7)

PG is a protecting group.
R₁ is methyl, phenyl, p-tolyl, p-bromophenyl, p-nitrophenyl.

To an appropriately protected 4-hydroxymethyl starting material (5) in basic solution, prepared substantially as described above, is added a aryl sulfonate, such as p-nitrobenzenesulfonyl chloride, to form intermediate (6). As in I(a) above, the sulfonylation reaction can be conducted in a polar organic solvent such as methylene chloride, starting at reduced temperatures of about 0° C. to about 25° C. for 1 to 24 hours.

Intermediate (6) is converted to the thiotetrazole by displacement of the sulfonate with 5-mercaptotetrazole, which reacts exclusively at the sulfur. The displacement reaction can be conducted in a polar organic solvent such as acetonitrile in the presence of triethylamine at temperatures up to reflux for about 2–8 hours. Hydrolysis again produces the desired compound (7).

Compounds where n is 1 can be prepared as follows:

Scheme I(c)

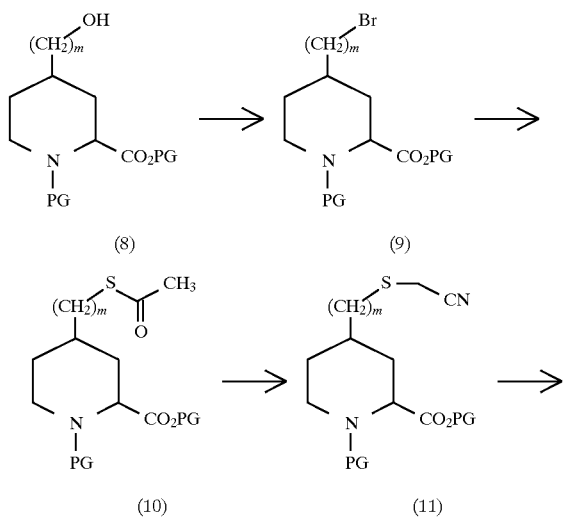

Scheme I(c) -continued

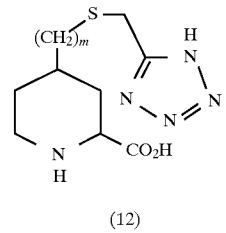

(12)

PG is a protecting group.

An appropriately protected starting material (8) may be reacted at temperatures from about 0° C. to room temperature with an appropriate halogenating agent such as triphenylphosphine dibromide in a solvent such as dichloromethane in the presence of a base such as pyridine. The halogen in the intermediate (9) can be displaced with potassium thioacetate in a polar solvent such as acetonitrile. Conversion to the cyanomethylthio intermediate (10) can be accomplished using a metal alkoxide such as methanol in the presence of a haloacetonitrile such as bromoacetonitrile at temperatures ranging from 0° C. to reflux of the solvent. Conversion to the tetrazole can then be accomplished by reaction with azido tri-n-butylstannane, either neat or in an aromatic solvent such as toluene as described in Scheme I(a) above, followed by hydrolysis of the protected carboxyl group to afford the deprotected final product (12).

Scheme II

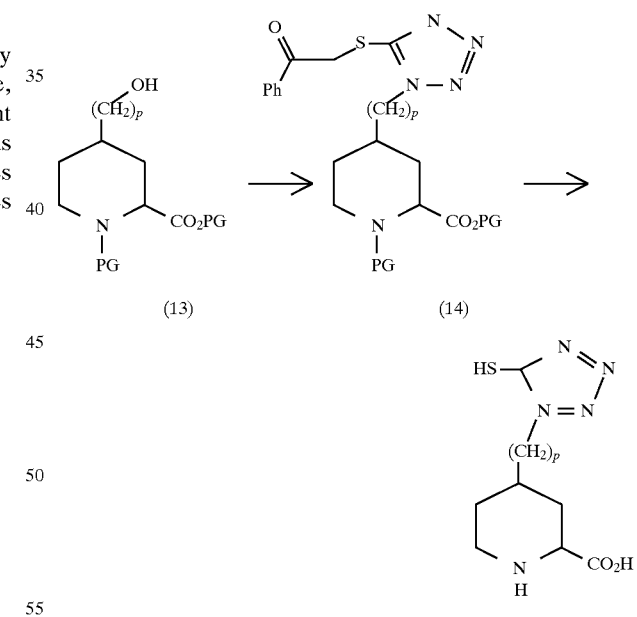

P=0–3

Scheme II illustrates the synthesis of a 5-mercapto tetrazole with no bridging atoms. The starting material (13) with an appropriately protected 5-mercaptotetrazole, such as S-phenacyltetrazole, under Mitsunobu conditions will give the fully protected intermediate (14). This reaction can be conducted in an aprotic polar solvent such as tetrahydrofuran in the presence of triphenylphosphine and diethylazodicarboxylate at temperatures ranging from −78° C. to room temperature for 1 to 24 hours. (The phenacyl group is removed photolytically by treatment with zinc and a strong acid (15).) Then the material is hydrolyzed to form the desired compound (15). When p=0, starting with the 2,4-cis isomer of compound (13) one obtains the 2,4-trans isomer of compound (15), and starting with the 2,4-trans isomer of compound (13) one obtains the 2,4-cis isomer of compound (15).

Scheme III

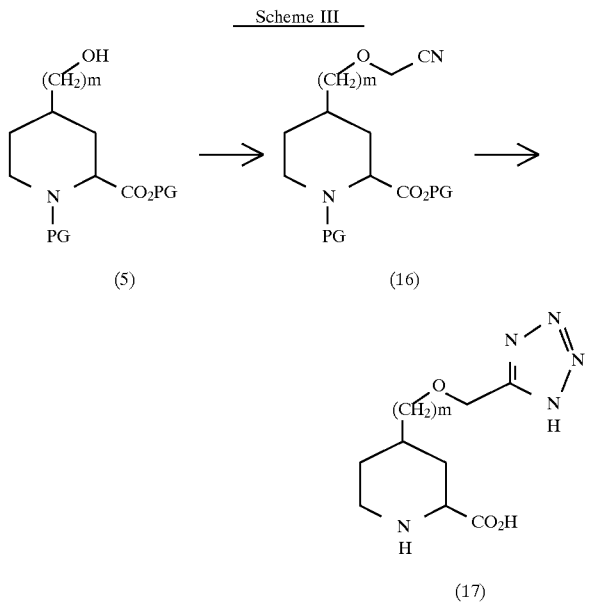

Scheme III illustrates the synthesis of compounds where X is oxygen, m is 0 or 1 and n is 1. In Scheme III, the (cyanomethyl)oxy group is introduced by first conversion of the alcohol group in (5) to an alkoxymethylether, such as methoxyethoxymethyl (MEM) or methoxymethyl (MOM), using a reagent such as methoxyethoxymethyl chloride, in the presence of a tertiary amine base such as diisopropyl-N-ethyl amine. The reaction may be conducted in an organic solvent such as dichloromethane at room temperature for about 1–2 days. This latent oxonium ion source is then converted to the (cyanomethyl)oxy group by reacting the MEM or MOM ether with cyanotrimethylsilane in the presence of a Lewis acid catalyst such as boron trifluoride diethyl etherate, using an organic solvent, such as dichloromethane. The reaction is conducted at temperatures ranging from −78° C. to room temperature, and is substantially complete in 30 minutes to 24 hours. This produces intermediate (16), which may readily be converted to the tetrazole, and deprotected as described in Scheme I(a) to form desired compound (17).

Scheme IV illustrates the formation of 4-methoxyimino-bridged compound (21):

Scheme IV

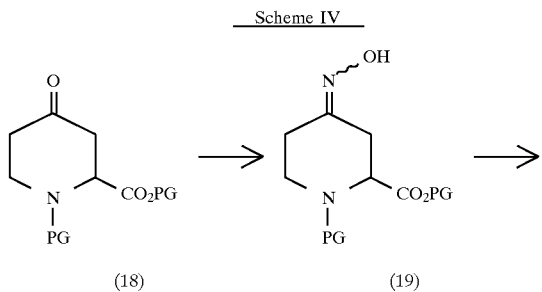

-continued
Scheme IV

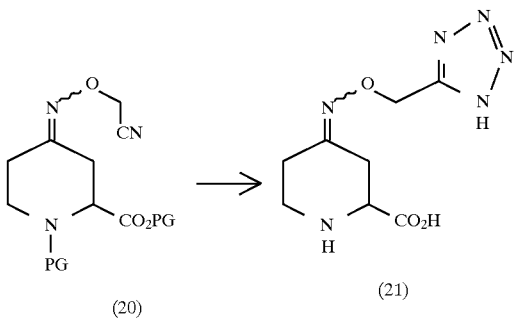

A 4-oxo protected piperidine carboxylic acid (18) is first reacted with a hydroxylamine salt such as hydroxylamine hydrochloride to form the 4-hydroxyimino intermediate (19). The reaction is conducted at ambient temperatures in an alcoholic solvent such as ethanol and is complete in about 1 to 8 hours. This intermediate is converted to the ((cyanoalkyl)oxy)imino intermediate (20) by reacting (19) with a cyanoalkylhalide reagent such as bromoacetonitrite in a polar aprotic solvent such as dimethylformamide. Finally, the tetrazole ring is formed as described in Scheme 1(a), and hydrolysis again yields the desired compound (21).

The reaction product may be separated from the reaction mixture obtained as above according to any conventional means in the art. For example, the reaction product can be isolated by such means as concentration of the reaction mixture followed by separation by recrystallation or chromatography.

In order to preferentially prepare one optical isomer over its enantiomer, the skilled practitioner may prepare the mixture of enantiomers and then separate the two enantiomers. A commonly employed method for the resolution of the racemic mixture (or mixture of enantiomers) into the individual enantiomers is to first convert the enantiomers to diastereomers by way of forming a salt with an optically active acid or base. These diastereomers can then be separated using differential solubility, fractional crystallization, chromatography, or like methods. Further details regarding resolution of enantiomeric mixtures can be found in J. Jacques, et al., *Enantiomers, Racemates, and Resolutions*, (1991).

The pharmaceutically acceptable salts of the invention are typically formed by reacting a compound of this invention with an equimolar or excess amount of salt forming reagent. The reactants are generally combined in a mutual solvent such as diethyl ether, benzene, ethanol or water and the salt normally precipitates out of solution within about one hour to 10 days, and can be isolated by filtration.

The starting compounds for each scheme are well known and commercially available or may be readily prepared by known techniques from commercially available starting materials.

The following Examples further illustrate the compounds of this invention and the methods used to synthesize them. These examples are illustrative only and should not be construed as limiting the invention in any way.

GENERAL EXPERIMENTAL

All solvents and reagents were used as obtained. Field desorption mass spectroscopy (FDMS) was performed using either a VG 70SE or a Varian MAT 731 instrument. Fast atom bombardment mass spectroscopy (FABMS) were performed using a ZAB-2SE instrument. The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 mL of 10% aqueous sulfuric acid] and then heated on a hot plate). Elemental analyses for carbon, hydrogen and nitrogen were determined on a Control Equipment Corporation 440 Elemental Analyzer. "Flash silica gel filtration" refers to chromatography on silica gel in a sintered glass funnel. The material to be chromatographed is dissolved in either dichloromethane or diethyl ether and preabsorbed onto silica gel (4–5 grams of silica gel 60 (230–400 mesh) per gram of material). The resultant slurry is concentrated in vacuo to a free-flowing powder. This material is added to a sintered glass funnel containing approximately 8–10 grams of silica gel 60 (230–400 mesh) per gram of material. Sand is placed carefully on top of the two silica gel layers, which are then eluted with the appropriate solvent, applying vacuum filtration. "Flash chromatography" (Still, W. C.; Kahn, M.; Mitra, A. *J. Org. Chem.* 1978, 43, 2923) refers to chromatography on 230–400 mesh Silica Gel 60, using the amount of silica gel and solvent of elution referred to parenthetically in the text. "Cation exchange chromatography" refers to ion exchange with Dowex 50X-8 (100–200) resin ($H^+$ form). The resin is prepared by washing (in a coarse porosity sintered glass funnel) with water, then methanol, then water, then 3N ammonium hydroxide ($pH^3$ 12), then water, then 1N HCl ($pH^2$ 1), then water until the pH is neutral. The resin is packed into a glass column in water, and the compound (which is dissolved in water at a pH between 2 and 7) was slowly loaded onto the resin, then the column is washed with water until the pH is neutral, then 50% aqueous THF, then water. The compound is eluted off of the resin with 10% aqueous pyridine, and product containing fractions (which are detected with ninhydrin stain on a TLC plate) are combined and concentrated in vacuo. Water is added and the mixture concentrated in vacuo. This procedure is repeated to ensure complete removal of pyridine. "Anion exchange chromatography" refers to anion exchange with Bio-Rad AG1-X8 anion exchange resin (hydroxide form). The resin (obtained in acetate form) was prepared by washing (in a coarse porosity sintered glass funnel) with water, then methanol, then water, then twice with 1N sodium hydroxide (converts to the hydroxide form), then water until pH 7. The resin was packed into a glass column in water, and the compound (which is dissolved in water at a pH between 9 and 12) is slowly loaded onto the resin, then the column washed with water until the pH is neutral, then 50% aqueous THF, then water. The compound is eluted off of the resin with 3N aqueous acetic acid, and product containing fractions (which are detected with ninhydrin stain on a TLC plate) are combined and concentrated in vacuo. "Reverse phase chromatography" refers to chromatography using Waters NOVAPAK $C_{18}$ reverse phase packing in a 40×300 mm column on a Waters LC System 3000 containing a radial compression module. Chelex 100 refers to a chelating ion exchange resin (100–200 mesh, $Na^+$ form), which is used as obtained to remove divalent cations, e.g., zinc. Reactions subjected to sonication employed a Heat Systems LXZ20 Sonication Ultrasonic Processor.

EXAMPLE 1

2SR,4RS-4-(((1H-Tetrazol-5-yl)methyl)oxy) piperidine-2-carboxylic acid

A. Ethyl 2SR,4RS-4-hydroxy-N-(methoxycarbonyl) piperidine-2-carboxylate

A solution of 6.1 g (22.1 mmol) of ethyl 2SR,4RS-4-hydroxy-N-(t-butoxycarbonyl)piperidine-2-carboxylate in 20 mL of dichloromethane and 10 mL of trifluoroacetic acid was stirred 1 hour at room temperature, then concentrated in vacuo. 25 mL of dichloromethane was added and the mixture was again concentrated in vacuo. The residue was dissolved in 50 mL of dichloromethane and cooled to 0° C., then treated with 11.6 mL (8.6 g, 66.4 mmol) of diisopropyl-N-ethyl amine and 1.9 mL (2.3 g, 24.3 mmol) of methyl chloroformate. After 1.5 hr at 0° C., the mixture was diluted with 100 mL of diethyl ether and washed twice with 50 mL each of 10% aqueous sodium bisulfate and once with 50 mL of saturated aqueous sodium bicarbonate, then dried ($MgSO_4$), filtered and concentrated in vacuo. Chromatography (250 g silica gel, 75% ethyl acetate/hexane) of the residue afforded 2.9 g (57%) of the title compound.

B. Ethyl 2SR,4RS-4-((cyanomethyl)oxy)-N-(methoxycarbonyl)piperidine-2-carboxylate A solution of 2.8 g (12.0 mmol) of the compound from Example 1A, 2.8 mL (3.0 g, 24.0 mmol) of ((methoxy)ethoxy)methyl chloride, 6.4 mL (4.8 g, 36.7 mmol) of diisopropyl-N-ethyl amine and 0.05 g (0.4 mmol) of 4-dimethylaminopyridine in 35 mL of dichloromethane was stirred 24 hr at room temperature, then treated with an additional 5 mL (3.7 g, 28.7 mmol) of diisopropyl-N-ethyl amine and 1.4 mL (1.5 g, 12.0 mmol) of (((2-methoxy)ethoxy)methoxy)methyl chloride. After 24 hr more at room temperature, the reaction was diluted with 100 mL of diethyl ether, washed three times with 50 mL each of 10% aqueous sodium bisulfate, then dried ($MgSO_4$), filtered and concentrated in vacuo to afford ethyl 2SR,4RS-4-(((2-methoxy)ethoxy)methyl)oxy)-N-methoxycarbonylpiperidine-2-carboxylate. This material was dissolved in 35 mL of dichloromethane, treated with 7.2 mL (5.4 g, 53.9 mmol) of cyanotrimethylsilane, cooled to 0° C., then treated with 4.4 mL (5.1 g, 35.9 mmol) of boron trifluoride diethyl etherate. After 30 minutes at room temperature, the mixture was carefully quenched with 100 mL of 10% aqueous potassium carbonate, then diluted with 100 mL of diethyl ether. The organic layer was separated and the aqueous layer extracted once with 50 mL of diethyl ether. The combined organics were washed twice with 50 mL each of 10% aqueous sodium bisulfate, then dried ($MgSO_4$), filtered and concentrated in vacuo. Chromatography (150 g silica gel, 50% ethyl acetate/hexane) of the residue afforded 2.3 g (70%) of the title compound.

C. A solution of 2.2 g (8.1 mmol) of the compound from Example 1B and 6.0 g (18.1 mmol) of azido-tri-n-butylstannane was heated to 90° C. for 3 days, heated to 100° C. overnight with 50 mL of 6N hydrochloric acid. The mixture was cooled to room temperature, extracted three times with 50 mL each of diethyl ether, then the aqueous layer was concentrated in vacuo. Cation exchange chromatography of the residue afforded a solid that was filtered and washed with water, acetone and diethyl ether and dried in vacuo at 60° C. to afford 0.6 g (33%) of the title compound.

Analysis calculated for $C_8H_{13}N_5O_3$: % C, 42.29; % H, 5.77; % N, 30.82. Found: % C, 42.00; % H, 5.90; % N, 30.62.

Field Desorption Mass Spectrum: M+1=228.

EXAMPLE 2

2SR,4RS-4-((((1H-Tetrazol-5-yl)methyl)oxy) methyl)piperidine-2-carboxylic acid

A. Ethyl 2SR,4RS-4-(hydroxymethyl)-N-(methoxycarbonyl)piperidine-2-carboxylate

A solution of 2.5 g (10.4 mmol) of ethyl 2SR,4RS-4-(hydroxymethyl)-N-(t-butoxycarbonyl)piperidine-2-carboxylate in 25 mL of dichloromethane and 15 mL of trifluoroacetic acid was stirred 1 hour at room temperature, then concentrated in vacuo. 25 mL of dichloromethane was added and the mixture was again concentrated in vacuo. The residue was dissolved in 50 mL of dichloromethane and cooled to 0° C., then treated with 10.5 mL (7.7 g, 59.4 mmol) of diisopropyl-N-ethyl amine and 1.5 mL (1.9 g, 19.8 mmol) of methyl chloroformate. After 1.5 hr at 0° C., the mixture was diluted with 100 mL of diethyl ether and washed twice with 50 mL each of 10% aqueous sodium bisulfate and once with 50 mL of saturated aqueous sodium bicarbonate, then dried ($MgSO_4$), filtered and concentrated in vacuo. The residue was dissolved in methanol and stirred 30 min at 50° C., then concentrated in vacuo. Chromatography (200 g silica gel, 75% ethyl acetate/hexane) of the residue afforded 2.7 g (55%) of the title compound.

B. Ethyl 2SR,4RS-4-(((cyanomethyl)oxy)methyl)-N-(methoxycarbonyl)piperidine-2-carboxylate A solution of 2.5 g (10.4 mmol) of the compound from Example 2A, 1.8 mL (1.9 g, 15.5 mmol) of ((methoxy)ethoxy)methyl chloride, 3.6 mL (2.7 g, 20.7 mmol) of diisopropyl-N-ethyl amine and 0.05 g (0.4 mmol) of 4-dimethylaminopyridine in 30 mL of dichloromethane was stirred 24 hr at room temperature, then treated with an additional 3.6 mL (2.7 g, 20.7 mmol) of diisopropyl-N-ethyl amine and 1.8 mL (1.9 g, 15.5 mmol) of (((methoxy)ethoxy)methoxy)methyl chloride. After 6 hours more at room temperature, the reaction was diluted with 100 mL of diethyl ether, washed three times with 50 mL each of 10% aqueous sodium bisulfate, then dried ($MgSO_4$), filtered and concentrated in vacuo to afford ethyl 2SR,4RS-4-(((methoxy)ethoxy)methyl)oxy)-N-methoxycarbonylpiperidine-2-carboxylate. This material was dissolved in 35 mL of dichloromethane, treated with 6.2 mL (4.6 g, 46.6 mmol) of cyanotrimethylsilane, cooled to 0° C., then treated with 3.8 mL (4.4 g, 31.1 mmol) of boron trifluoride diethyl etherate. After 30 min at room temperature, the mixture was carefully quenched with 100 mL of 10% aqueous potassium carbonate, then diluted with 100 mL of diethyl ether. The organic layer was separated and the aqueous layer extracted once with 50 mL of diethyl ether. The combined organics were washed twice with 50 mL each of 10% aqueous sodium bisulfate, then dried ($MgSO_4$), filtered and concentrated in vacuo. Chromatography (150 g silica gel, 50% ethyl acetate/hexane) of the residue afforded 2.1 g (72%) of the title compound.

C. A solution of 2.0 g (7.1 mmol) of the compound from Example 2B and 5.7 g (17.2 mmol) of azido-tri-n-butylstannane was heated to 90° C. for 3 days, the heated to 100° C. overnight with 50 mL of 6N hydrochloric acid. The mixture was cooled to room temperature, extracted three times with 50 mL each of diethyl ether, then the aqueous layer was concentrated in vacuo. Cation exchange chromatography of the residue afforded a solid that was filtered and washed with water, acetone and diethyl ether and dried in vacuo at 60° C. to afford 1.2 g (71%) of the title compound.

Analysis calculated for $C_9H_{15}N_5O_3 \cdot 0.75\ H_2O$: % C, 42.43; % H, 6.53; % N, 27.49. Found: % C, 42.77; % H, 6.44; % N, 27.57.

Field Desorption Mass Spectrum: M=241.

EXAMPLE 3

E and Z 2SR-4-(O-(1H-Tetrazol-5-yl)methyl) ketoximino)piperidine-2-carboxylic acid A. E and Z ethyl 2SR-4-ketoxoimino-N-(t-butoxycarbonyl) piperidine-2 -carboxylate A room temperature suspension of 6.6 g (24.4 mmol) of ethyl 2SR-4-oxo-N-(t-butoxycarbonyl)piperidine-2-carboxylate, 2.4 g (29.3 mmol) of sodium acetate and 2.0 g (29.3 mmol) of hydroxylamine hydrochloride in 25 mL of ethanol was stirred 7.5 hr, then filtered through diatomaceous earth. The filtrate was diluted with 100 mL of diethyl ether and washed with a mixture of 50 mL of brine and 50 mL of 10% aqueous sodium bisulfate. The organic layer was separated, washed three times with 10 mL each of water, then dried (NaCl, $MgSO_4$), filtered and concentrated in vacuo. Silica gel filtration (28 g; 3.5×9.5; gradient 11:2 to 5:2 toluene:ethyl acetate) afforded 3.1 g (44%) of the title compound.

B. E and Z ethyl 2SR-4-(O-(cyanomethyl)ketoxoimino)-N-(t-butoxycarbonyl)piperidine-2-carboxylate To a −40° C. solution of 0.96 g (3.3 mmol) of the compound from example 3A and 0.45 g (3.8 mmol) of bromoacetonitrile in 5 mL of dimethylformamide was added 0.15 g (3.7 mmol) of sodium hydride. The mixture was stirred for 10 min at −40° C., 25 min and 7 hours at room temperature. The mixture was diluted with 100 mL of diethyl ether and washed with 100 mL of water, then the organic layer separated and the aqueous layer extracted three times with 50 mL each of diethyl ether. The combined organics were dried (NaCl, $MgSO_4$), filtered and concentrated in vacuo. Silica gel filtration (6 g; 2.5×6.5; gradient 11:1 to 3:1 hexane:diethyl ether) afforded 0.59 g (55%) of the title compound.

C. A solution of 0.59 g (1.8 mmol) of the compound from example 3B and 0.75 g (2.2 mmol) of azido-tri-n-butylstannane was heated to 88° C. for 7.5 hr. To the mixture was added 4 mL of diethyl ether and 0.5 mL of 5N hydrochloric acid, and this was stirred for 10 min at room temperature. The mixture was diluted with 20 mL of diethyl ether, washed with a mixture of 15 mL of water and 5 mL of 10% aqueous sodium bisulfate, then the organic layer was separated and washed three times with 10 mL each of water. The organic layer was diluted with hexane, cooled to −78° C., and the resulting solid was broken-up, the solution allowed to settle and the supernatant decanted. This material was dried in vacuo overnight, then the resulting oil was dissolved in 50 mL of diethyl ether, dried ($MgSO_4$), filtered and concentrated in vacuo to afford 0.44 g of E and Z ethyl 2SR-4-(O-((1H-tetrazol-5-yl)methyl)ketoxoimino)-N-t-butoxycarbonylpiperidine-2-carboxylate. This material was dissolved in 1.8 mL of 2N sodium hydroxide, 2 mL of dioxane and 1 mL of water and stirred 7.2 hr at room temperature. The mixture was diluted with 25 mL of ethyl acetate and washed with 25 mL of water. The organic layer was separated and the aqueous layer extracted four times with 10 mL each of ethyl acetate. The aqueous layer was brought to pH 2 with 1N hydrochloric acid, extracted once with 50 mL and four times with 10 mL each of ethyl acetate, then dried (NaCl, $MgSO_4$), filtered and concentrated in vacuo to afford 0.30 g of E and Z 2SR-4-(O-((1H-tetrazol-5-yl)methyl)ketoxoimino)-N-t-butoxycarbonylpiperidine-2-carboxylic acid. This material was treated with 0.2 g (1.0 mmol) of iodotrimethylsilane in 6 mL of dichloromethane for 30 minutes at room temperature, then concentrated in vacuo. An additional 25 mL of dichloromethane was added and the material again concentrated in vacuo, then the residue suspended in dichloromethane and filtered, washing with dichloromethane. Anion exchange chromatography afforded 0.10 g (21%) of the title compound.

Analysis calculated for $C_9H_{15}N_5O_3 \cdot 0.75\ H_2O$: % C, 42.43; % H, 6.53; % N, 27.49. Found: % C, 42.77; % H, 6.44; % N, 27.57.

Field Desorption Mass Spectrum: M=241.

EXAMPLE 4

2SR,4SR-4-((1H-Tetrazol-5-yl)thio)piperidine-2-carboxylic acid

A. Ethyl 2SR,4RS-4-hydroxy-N-(t-butoxycarbonyl)piperidine-2-carboxylate

A solution of ethyl 2SR-4-oxo-N-(t-butoxycarbonyl)piperidine-2-carboxylate (22.6 mmole, 6.1 g) in methanol (150 mL) was cooled to −35° C. and treated with cerium chloride (22.6 mmole, 8.4 g). After stirring at −35° C. for five min, sodium borohydride (22.6 mmole, 0.90 g) was added directly to the suspension. After 2.5 hr, additional sodium borohydride (22.6 mmole, 0.8969 g) was added to the reaction mixture. After an additional 1.4 hours at −35° C. and 1 hr at room temperature, the suspension was concentrated in vacuo. The residue was dissolved in 150 mL of dichloromethane and washed with 150 mL of water. The aqueous layer was extracted with ethyl acetate (3×50 mL), then acidified and extracted with additional ethyl acetate (50 mL). The combined organics were dried ($NaCl/MgSO_4$), filtered and concentrated in vacuo to afford an oil (3.6 g). Flash silica gel filtration (hexane/ethyl acetate gradient: 6/1,1 L; 5/1,1 L; 4/1,1 L; 2/1,1 L; then 1:1; 70 mL fractions) afforded 5.1 g (83%) of the title compound (10:1 mixture of 2SR,4RS:2SR,4SR diastereomers).

Analysis calculated for $C_{13}H_{23}NO_5$: % C, 57.13; % H, 8.48; % N, 5.12. Found: % C, 56.90; % H, 8.39; % N, 4.96.

Field Desorption Mass Spectrum: M=273.

B. Ethyl 2SR,4RS-4-(p-toluenesulfonyl)-N-(t-butoxycarbonyl)piperidine-2-carboxylate A solution of the compound from Example 4A (3.9 mmole, 1.06 g), pyridine (11.7 mmole, 0.92 g), 4-(N,N-dimethylamino)pyridine (DMAP) (0.2 mmole, 0.02 g) and p-toluenesulfonyl chloride (10.9 mmole, 2.1 g) in dichloromethane (4 mL) was stirred at room temperature for 96 hours. The reaction mixture was diluted with dichloromethane (10 mL) and washed with 10% aqueous sodium bisulfate (3×25 mL). The organic layer was washed with saturated aqueous sodium bicarbonate (25 mL), then dried (NaCl) and filtered. Flash silica gel filtration. (10% ethyl acetate/hexane) afforded 1.2 g (71%) of the title compound.

Analysis calculated for $C_{20}H_{29}NO_7S$: % C, 56.19; % H, 6.84; % N, 3.27. Found: % C, 55.97; % H, 7.08; % N, 3.51.

Field Desorption Mass Spectrum: M+1=428.

C. Ethyl 2SR,4SR-4-thiocyanato-N-(t-butoxycarbonyl)piperidine-2-carboxylate

A suspension of the compound from Example 4B (2.7 mmole, 1.14 g) and potassium thiocyanate (8.0 mmole, 0.77 g) in dimethylformamide (3 mL) was heated at 78° C. for 24 hr and 26.5 hr at room temperature. At this time, 18-crown-6 (0.3 mmole, 0.07 g) was added and the mixture was heated for 5 hr at 78° C. The mixture was cooled to room temperature, diluted with diethyl ether (30 mL) and filtered, the solids washed with diethyl ether, then the filtrate was concentrated in vacuo. Flash silica gel filtration (hexane/diethyl ether gradient: 95/5, 1 L; 92.5/7.5, 1 L; 90/10, 1 L; then 85/15, collecting 13 mL fractions) afforded 0.33 g (39%) of the title compound.

Analysis calculated for $C_{14}H_{22}N_2O_4S$: % C, 53.48; % H, 7.05; % N, 8.91. Found: % C, 53.44; % H, 7.11; % N, 9.07.

Field Desorption Mass Spectrum: M+1=315

D. Ethyl 2SR,4SR-4-((1H-tetrazol-5-yl)thio)-N-(t-butoxycarbonyl)piperidine-2-carboxylate A neat solution of the compound from Example 4C (0.8 mmole, 0.25 g) and azido tri-n-butylstannane (1.0 mmole, 0.33 g) was heated for 8 hr at 72° C. The reaction mixture was cooled to room temperature and treated with 1N HCl (1.17 mmole, 1.17 mL). After 15 min the mixture was treated with diethyl ether (20 mL), water (20 mL) and 10% aqueous sodium bisulfate (10 mL), the layers separated and the organic layer washed with water (2×10 mL). The organic layer was treated with water (10 mL), the pH of the biphasic mixture was adjusted to 10 with 1N sodium hydroxide, then the layers were separated and the organic layer washed with water (3×5 mL). The combined aqueous washes were treated with diethyl ether (20 mL), acidified with 10% aqueous sodium bisulfate (15 mL), the layers separated and the aqueous layer extracted with diethyl ether (3×10 mL). The combined organic extracts were dried ($NaCl/MgSO_4$), filtered, and concentrated in vacuo to afford 0.18 g of crude product.

The crude product was subjected to reverse layer chromatography. Product eluted with acetonitrile:water:acetic acid (45:54:1). Fractions containing desired product concentrated in vacuo to afford 0.14 g of the title compound. This material contained some impurities and was used in the next reaction without further purification.

$^1$H NMR (DMSOd6): δ 4.51 (bs, 1H), 4.15 (bs, 1H), 4.02–3.92 (2H), 3.73 (bd, 1H), 3.18–3.02 (m, 1H), 2.41 (bs, 1H), 2.29–2.23 (m, 1H), 2.03–1.92 (m, 1H), 1.79 (m, 1H), 1.33 (s, 9H), 0.99 (t, 3H).

Field Desorption Mass Spectrum: M+1=358.

E. A solution of the compound from Example 4D (0.4 mmole, 0.14 g), ethanol (2 mL), water (1 mL) and 5N HCl (10 mL) was stirred at room temperature for 1 hr, 5.5 hours at reflux and overnight at room temperature. The solution was concentrated in vacuo, treated with water, and the pH adjusted to 9 with 1N sodium hydroxide. Cation exchange chromatography gave 0.06 g (69%) of the title compound.

Analysis calculated for $C_7H_{11}N_5O_2S \cdot 0.5\ H_2O \cdot 0.45 \cdot C_5H_5N$: % C, 40.57; % H, 5.24; % N, 27.87. Found: % C, 40.48; % H, 5.24; % N, 27.76.

Fast Atom Bombardment Mass Spectrum: M+1=230

EXAMPLE 5

2SR,4S-4-((1H-tetrazol-5-yl)thio)piperidine-2-carboxylic acid

A. Ethyl 2SR,4SR-4-(p-toluenesulfonyl)-N-(t-butoxycarbonyl)piperidine-2-carboxylate A solution of ethyl 2SR,4SR-4-hydroxy-N-(t-butoxycarbonyl)piperidine-2-carboxylate (48 mmole, 13.1 g), pyridine (144 mmole, 11.4 g), DMAP (2.4 mmole, 0.29g) and p-toluenesulfonyl chloride (134.5 mmole, 25.7 g) in dichloromethane (48 mL) was stirred at 120 hours at room temperature. The reaction mixture was diluted with dichloromethane (100 mL) and washed with 10% aqueous sodium bisulfate (4×50 mL), 10% aqueous potassium carbonate (2×50 mL), and brine (50 mL). The organic layer was dried (NaCl), filtered and concentrated in vacuo to afford 35.5 g of an oil. Flash silica gel filtration (hexane/ethyl acetate gradient: 9/1, 4.8 L; 4/1, 1.6 L; 7/3, 1.6 L) to afford 15.9 g (78%) of the title compound.

Analysis calculated for $C_{20}H_{29}NO_7S$: % C, 56.19; % H, 6.84; % N, 3.28. Found: % C, 56.24; % H, 6.79; % N, 3.49.

Field Desorption Mass Spectrum: M=427

B. Ethyl 2SR,4RS-4-thiocyanato-N-(t-butoxycarbonyl)piperidine-2-carboxylate

A suspension of the compound from Example 5A (37.3 mmole, 15.9 g) and potassium thiocyanate (111.8 mmole, 10.9 g) in N,N-dimethylformamide (37 mL) was heated to 65° C. for 39.5 hr, then cooled to room temperature. The mixture was diluted with diethyl ether (350 mL), filtered, the solid washed with diethyl ether (50 mL) and the filtrate concentrated in vacuo. The residue was dissolved in dichloromethane and washed with 10% aqueous potassium carbonate (3×50 mL) and brine (1×50 mL). The organic layer was dried (NaCl), filtered and concentrated in vacuo to afford 12.0 g of an oil. Flash silica gel filtration (hexane/diethyl ether gradient: 92.5/7.5, 2 L; 85/15, 4.5 L; 78/2, 2 L) afforded 5.0 g (43%) of the title compound.

Analysis calculated for $C_{14}H_{22}N_2O_4S$: % C, 53.48; % H, 7.05; % N, 8.91. Found: % C, 53.27; % H, 7.07; % N, 8.62.

Field Desorption Mass Spectrum: M=314

C. Ethyl 2SR,4RS-4-((1H-tetrazol-5-yl)thio)-N-(t-butoxycarbonyl)piperidine-2-carboxylate A solution of the compound from Example 5B (15.8 mmole, 4.96g) and azido tri-n-butylstannane (19.7 mmole, 6.55 g) was heated at 78° C. for 2 hr, and room temperature for 2.5 hr. To the mixture was added diethyl ether (37 mL) and 5N hydrochloric acid (23.3 mmole, 4.6 mL). After 35 minutes, diethyl ether (100 mL), water (100 mL) and 10% aqueous sodium bisulfate (25 mL) were added, the layers separated, and the organic layer washed with 10% aqueous sodium bisulfate (3×25 mL). The organic layer was treated with water (100 mL), the pH of biphasic mixture adjusted to 10 with 1N sodium hydroxide, then the organic layer was separated and washed with water (3×10 mL). The combined aqueous washes were treated with ethyl acetate (50 mL), the pH adjusted to 2, the layers separated and the aqueous layer extracted with ethyl acetate (3×10 mL). The combined organic layers were dried (NaCl/MgSO$_4$), filtered and concentrated in vacuo. The crude product was subjected to reverse phase chromatography. Product eluted with acetonitrile:water:acetic acid (45:54:1). Fractions containing desired product concentrated in vacuo to afford 1.83 g (32%) of the title compound.

Analysis calculated for $C_{14}H_{23}N_5O_4S$: % C, 47.04; % H, 6.49; % N, 19.59. Found: % C, 46.85; % H, 6.53; % N, 19.31.

Field Desorption Mass Spectrum: M+1=358

D. A solution of the compound from Example 5C (5.1 mmole, 1.83 g) in ethanol (12 mL), water (7 mL) and 5N HCl (10 mL) was stirred at room temperature for 1 hr, then additional 5N HCl (40 mL) was added and the mixture stirred at room temperature for 19.5 hr and at reflux for 4 hr. The mixture was cooled to room temperature and concentrated in vacuo. Cation exchange chromatography of the residue afforded 0.73 g (62%) of the title compound.

Analysis calculated for $C_7H_{11}N_5O_2S \cdot 0.5\ H_2O \cdot 0.2\ C_5H_5N$: % C, 37.82; % H, 5.16; % N, 28.66. Found: % C, 38.08; % H, 5.10; % N, 28.55.

Fast Atom Bombardment Mass Spectrum: M+1=230

EXAMPLE 6

2SR,4RS-4-(5-mercapto-1H-tetrazol-1-yl)piperidine-2-carboxylate

A. Ethyl 2SR,4RS-4-(5-((2-oxo-2-phenylethyl)thio)-1H-tetrazol-1-yl)-N-(t-butoxycarbonyl)piperidine-2-carboxylate To a −78° C. solution of ethyl 2SR,4SR-4-hydroxy-N-(t-butoxycarbonyl)piperidine-2-carboxylate (37.3 mmole, 10.2 g), triphenylphosphine (41.0 mmole, 10.8 g) and 5-(2-oxo-2-phenylethyl)thio-1H-tetrazole (41.0 mmole, 9.0 g) in tetrahydrofuran (60 mL) and acetonitrile (40 mL) was added diethyl azodicarboxylate (41.0 mmole, 7.2 g) over 20 min. The solution was then subjected to constant sonication at the level 4 setting. The mixture was stirred 3 hours at −78° C., 3 hr at −15° C. and 11 hr at room temperature, then concentrated in vacuo. The residue was suspended in toluene (50 mL), filtered, the solid washed with toluene (20 mL) and the filtrate concentrated in vacuo. The residue was dissolved in dichloromethane (200 mL) and washed with 0.1N sodium hydroxide (5×100 mL). The organic layer was dried (MgSO$_4$), filtered and concentrated in vacuo. Flash silica gel filtration. (dichloromethane (3.5 L), then hexane/ethyl acetate gradient: 7/3, 3 L; 1/1, 3 L). afforded the crude title compound. This material was subjected to reverse phase chromatography (C-18 Nova column) eluting with methanol:water:acetic acid (70:29:1) to afford 1.4 g (8%) of the title compound.

Analysis calculated for $C_{22}H_{29}N_5O_5S$: % C, 55.56; % H, 6.15; % N, 14.73. Found: % C, 55.53; % H, 6.08; % N, 14.81.

Field Desorption Mass Spectrum: M+1=476

B. Ethyl 2SR,4RS-4-(5-mercapto-1H-tetrazol-1-yl)-N-(t-butoxycarbonyl)piperidine-2-carboxylate A solution of the compound from Example 6A (2.4 mmole, 1.1 g) in degassed ethanol (245 mL) was subjected to photolysis (450 W mercury arc lamp, pyrex filter) under an argon atmosphere. After 3.5 hours the reaction was concentrated in vacuo, treated with dichloromethane (100 mL) and water (50 mL), and the pH adjusted from 3.0 to 7.3 with 1N sodium hydroxide. The layers were separated, and the organic layer was washed with water (3×25 mL). The combined aqueous washes were acidified with 10% aqueous sodium bisulfate (20 mL) and extracted with dichloromethane (1×50 mL; 3×25 mL). The organic layer from the sodium hydroxide washings was washed with 10% aqueous potassium carbonate (3×20 mL). These aqueous washes were combined and acidified with 10% aqueous sodium bisulfate (60 mL) and extracted with dichloromethane (3×20 mL). The organic extracts obtained from both series of extractions of the aqueous acidic washes were combined, dried (MgSO$_4$), filtered and concentrated in vacuo to afford 0.57 g (67%) of the title compound.

$^1$H NMR(DMSO-d6): d 4.95–4.85 (m, 1H), 4.53–4.44 (m, 1H), 4.24–3.95 (m, 3H), 3.13–2.88 (m, 1H), 2.43–2.36 (m, 1H), 2.11–1.95 (m, 2H), 1.91–1.79 (m, 1H), 1.38–1.34 (d, 9H), 1.22–1.17 (t, 3H).

Field Desorption Mass Spectrum: M=357

C. A solution of the compound from Example 6B (1.6 mmole, 0.56 g) in ethanol (2 mL) was treated with 5N hydrochloric acid (40 mL) was heated to a boil until all of the ethanol had distilled off, then refluxed for 5.5 hr. The solution was cooled to room temperature and the resulting solid was collected by filtration, washed with acetone (30 mL) and diethyl ether (60 mL) and dried in vacuo overnight to afford 0.35 g (84%) of the title compound.

Analysis calculated for $C_7H_{12}ClN_5O_2S$: % C, 31.64; % H, 4.55; % N, 26.36. Found: % C, 31.37; % H, 4.45; % N, 26.10.

Fast Atom Bombardment Mass Spectrum: M-HCl=230

EXAMPLE 7

2SR,4RS-4-(5-mercapto-2H-tetrazol-2-yl)piperidine-2-carboxylic acid

A. Ethyl 2SR,4RS-4-hydroxy-N-(t-butoxycarbonyl)piperidine-2-carboxylate

A mixture of diethyl azodicarboxylate (51.1 mmole, 8.9 g) and triphenylphosphine (51.1 mmole, 13.4 g) in tetrahydrofuran (125 mL) was stirred at room temperature for 5 min, then treated with triflouroacetic acid (50.0 mmole, 5.7 g) over a two minute period. This mixture was then added to a mixture of ethyl 2SR,4SR-4-hydroxy-N-(t-butoxycarbonyl)piperidine-2-carboxylate (39.3 mmole, 10.8 g) in tetrahydrofuran (45 mL) over a five minute period. Five min after addition the reaction mixture was treated with sodium benzoate (51.9 mmole, 7.5 g). The mixture was stirred 24 hr at room temperature, then concentrated in vacuo. The residue was triturated with 10% ethyl acetate/cyclohexane (500 mL), then filtered through a two inch silica gel pad and washed with 10% ethyl acetate/cyclohexane (1.1 L). The filtrate was concentrated in vacuo to afford ethyl 2SR,4SR-4-(trifluoroacetoxy)-N-(t-butoxycarbonyl)piperidine-2-carboxylate. This material was dissolved in ethanol (100 mL), added to a suspension of sodium (14 g-atoms, 0.34 g) and sodium benzoate (50 mmole, 7.2 g) in ethanol (170 mL) and stirred 25 hr at room temperature. The mixture was concentrated in vacuo and treated with dichloromethane (200 mL) and water (150 mL), then the pH adjusted from 12.6 to 9.0 with 1N hydrochloric acid, the layers separated, and the aqueous layer extracted with dichloromethane (3×50 mL). The combined organic layers were dried (NaCl/MgSO$_4$), filtered and concentrated in vacuo. Flash chromatography (gradient of hexane to 50% ethyl acetate/hexane) of the residue afforded 4.6 g (43%) of a 6/4 mixture of 2SR,4RS/2SR,4SR isomers (by $^1$H NMR) of the title compound.

Analysis calculated for $C_{13}H_{23}NO_5$: % C, 57.13; % H, 8.48; % N, 5.12. Found: % C, 56.87; % H, 8.76; % N, 5.24.

Field Desorption Mass Spectrum: M=273

B. Ethyl 2SR,4RS-4-(5-((2-oxo-2-phenylethyl)thio)-2H-tetrazol-2-yl)-N-(t-butoxycarbonyl)piperidine-2-carboxylate, ethyl 2SR,4SR-4-(5-((2-oxo-2-phenylethyl)thio)-1H-tetrazol-1-yl)-N-(t-butoxycarbonyl)piperidine-2-carboxylate and ethyl 2SR,4SR-4-(5-((2-oxo-2-phenylethyl)thio)2H-tetrazol-2-yl)-N-(t-butoxycarbonyl)piperidine-2-carboxylate A −55° C. suspension of the compound from Example 7A (16.7 mmole, 4.6 g), triphenylphosphine (18.4 mmole, 4.8 g) and 5-(2-oxo-2-phenylethyl)thio-1H-tetrazole (18.4 mmole, 4.0 g) in tetrahydrofuran (21 mL), was treated dropwise over 20 min with a solution of diethyl azodicarboxylate (18.4 mmole, 3.2 g) in tetrahydrofuran (18 mL). Additional tetrahydrofuran (10 mL), was added and the mixture then subjected to constant sonication at the level 4 setting for 2.5 hr at −55° C. and −15° C. for 5 hours. The suspension was treated with diatomaceous earth, filtered, and insolubles washed with methanol. After cooling the filtrate overnight at 0° C., the resulting solid was filtered and washed with tetrahydrofuran. The filtrate was reduced in volume, triturated with toluene (25 mL), the insoluble material was filtered, washing with toluene (10 mL) and the filtrate concentrated in vacuo. Flash chromatography of the residue (gradient of hexane to 25% ethyl acetate/hexane) afforded 1.3 g (17%) of ethyl 2SR,4RS-4-(5-((2-oxo-2-phenylethyl)thio)-2H-tetrazol-2-yl)-N-(t-butoxycarbonyl)piperidine-2-carboxylate, 1.1 g (13%) of ethyl 2SR,4SR-4-(5-((2-oxo-2-phenylethyl)thio)-1H-tetrazol-1-yl)-N-(t-butoxycarbonyl)piperidine-2-carboxylate (contaminated with 33 mol % of 1,2-dicarboethoxyhydrazine; used in subsequent reactions without further purification) and 3.3 g (43%) of ethyl 2SR,4SR-4-(5-((2-oxo-2-phenylethyl)thio)2H-tetrazol-2-yl)-N-(t-butoxycarbonyl)piperidine-2-carboxylate.

Ethyl 2SR,4RS-4-(5-((2-oxo-2-phenylethyl)thio)-2H-tetrazol-2-yl)-N-(t-butoxycarbonyl)piperidine-2-carboxylate Analysis calculated for $C_{22}H_{29}N_5O_5S$: % C, 55.56; % H, 6.15; % N, 14.73. Found: % C, 55.31; % H, 6.11; % N, 14.65.

Field Desorption Mass Spectrum: M=475.

Ethyl 2SR,4SR-4-(5-((2-oxo-2-phenylethyl)thio)-1H-tetrazol-1-yl)-N-(t-butoxycarbonyl)piperidine-2-carboxylate $^1$H NMR(DMSO-d6) δ: 7.99 (d, 2H), 7.66 (t, 1H), 7.53 (t, 2H), 5.10 (s, 2H), 4.80–4.75 (m, 1H), 4.55–4.51 (m, 1H), 3.90–3.66 (m, 3H), 3.63–3.44 (m, 1H), 2.33–2.29 (m, 2H), 2.13–2.05 (m, 2H), 1.34 (s, 9H), 1.03 (t, 3H).

Field Desorption Mass Spectrum: M+1=476.

Ethyl 2SR,4SR-4-(5-((2-oxo-2-phenylethyl)thio)2H-tetrazol-2-yl)-N-(t-butoxycarbonyl)piperidine-2-carboxylate $^1$H NMR (DMSO-d6) δ: 8.00 (d, 2H), 7.65 (t, 1H), 7.52 (t, 2H), 5.07–4.99 (m, 1H), 4.91 (s, 2H), 4.53–4.47 (m, 1H), 3.87–3.62 (m, 3H), 3.25–3.13 (m, 1H), 2.65 (d, 1H), 2.42–2.37 (m, 1H), 2.32–2.23 (m, 1H), 2.10–1.97 (m, 1H), 1.31 (s, 9H), 1.03 (t, 3H).

Field Desorption Mass Spectrum: M=475.

C. Ethyl 2SR,4RS-4-(5-mercapto-2H-tetrazol-2-yl)piperidine-2-carboxylate

A suspension of ethyl 2SR,4RS-4-(5-((2-oxo-2-phenylethyl)thio)-2H-tetrazol-2-yl)-N-(t-butoxycarbonyl)piperidine-2-carboxylate from Example 7B, (2.6 mmole, 1.2 g) and zinc dust (5.25 mmole, 0.35 g) in formic acid (9 mL) was stirred 48 hours at room temperature, then heated at 62° C. for 20 minutes. The mixture was cooled to room temperature and filtered though diatomaceous earth, washing with warm formic acid. The filtrate was concentrated in vacuo, then treated with water (30 mL) and diethyl ether (10 mL), the layers separated, and the aqueous layer extracted with diethyl ether (2×10 mL). The aqueous layer was concentrated in vacuo, treated with a slurry of Chelex 100 (approximately 20 mL) in water for 2 hr, then filtered, and the insolubles washed with water. The filtrate was concentrated in vacuo to afford 0.19 g (27%) of the title compound, used in subsequent reactions without further purification.

Field Desorption Mass Spectrum: M=257.

D. A solution of the compound from Example 7C (0.7 mmole, 0.19 g) was refluxed in 5N hydrochloric acid (20 mL) for 5.5 hr, then the solution was concentrated in vacua. The residue was dissolved in water, subjected to CHELEX 100 chromatography, and the material thus obtained was subjected to cation exchange chromatography to afford 0.03 g (12%) of the title compound.

Field Desorption Mass Spectrum: M=230.

EXAMPLE 8

2SR,4SR-4-(5-mercapto-1H-tetrazol-1-yl)piperidine-2-carboxylic acid

A. Ethyl 2SR,4SR-4-(5-mercapto-1H-tetrazol-1-yl)piperidine-2-carboxylate

A suspension of ethyl 2SR,4SR-4-(5-((2-oxo-2-phenylethyl)thio)-1H-tetrazol-1-yl)-N-(t-butoxycarbonyl)

piperidine-2-carboxylate from Example 7C (0.99 mmole, 0.47 g) and zinc dust (1.98 mmole, 0.13 g) in formic acid (3.5 mL) was stirred 48 hr at room temperature, then filtered though diatomaceous earth, washing with warm formic acid. The filtrate was concentrated in vacuo, treated with water (30 mL) and diethyl ether (10 mL), the layers separated and the aqueous layer extracted with diethyl ether (3×10 mL). The aqueous layer concentrated in vacuo and treated with a slurry of Chelex 100 (approximately 20 mL) in water for 2.2 hr, then filtered, and the insolubles washed with water. The filtrate was concentrated in vacuo to afford 0.12 g (47%) of the title compound, which contained diethyl hydrazine-1,2-dicarboxylate as an impurity, and was used without further purification.

$^1$H NMR (DMSO-d6) δ: 4.92–4.84 (m, 1H), 4.40 (dd, 1H), 4.18 (t, 2H), 3.44–3.40 (m, 1H), 3.17–3.07 (m, 1H), 2.41–2.36 (m, 1H), 2.10–1.89 (m, 3H), 1.12 (t, 3H).

Field Desorption Mass Spectrum: M=257.

B. A solution of the compound from Example 8A (0.4 mmole, 0.11 g) in 5N hydrochloric acid (20 mL) was heated to reflux for 5.5 hr, then cooled to room temperature and concentrated in vacuo to afford 0.08 g (68%) of the title compound as the hydrochloride salt.

Field Desorption Mass Spectrum: M−1=229.

EXAMPLE 9

2SR,4SR-4-(5-mercapto-2H-tetrazol-2-yl)piperidine-2-carboxylic acid

A. Ethyl 2SR,4SR-4-(5-mercapto-2H-tetrazol-2-yl)-N-(t-butoxycarbonyl)piperidine-2-carboxylate A solution of ethyl 2SR,4SR-4-(5-((2-oxo-2-phenylethyl)thio)2H-tetrazol-2-yl)-N-(t-butoxycarbonyl)piperidine-2-carboxylate from Example 7C (1.25 mmole, 0.60 g) in ethanol (200 mL) was subjected to photolysis (450 W mercury arc lamp, pyrex filter). After 4 hr of photolysis, the reaction was heated to 60° C. for 45 min, then concentrated in vacuo. The residue was treated with dichloromethane (25 mL) and water (10 mL), the pH adjusted from 2.8 to 6.8 with 1N sodium hydroxide, the layers separated and the aqueous layer extracted with dichloromethane (3×5 mL). To the aqueous layer was added ethyl acetate (20 mL), the pH adjusted from 7.1 to 2.3 with 1N hydrochloric acid, the layers separated and the organic layer dried (MgSO$_4$), filtered and concentrated in vacuo to afford 0.11 g (31%) of the title compound.

$^1$H NMR (DMSO-d6) δ: 5.07 (bs, 1H), 4.52 (m, 1H), 3.87–3.71 (m, 3H), 3.27–3.22 (bs, 1H), 2.72–2.68 (bd, 1H), 2.48–2.32 (m, 2H), 2.14–2.04 (m, 1H), 1.32 (s, 9H), 1.12 (t, 3H).

Field Desorption Mass Spectrum: M=357.

B. A solution of the compound from Example 9A (0.3 mmole, 0.10 g) in 5N hydrochloric acid (10 mL) was refluxed for 5.5 hours, then cooled to room temperature and concentrated in vacuo to afford 63 mg of the title compound as the hydrochloride salt.

Analysis calculated for C$_7$H$_{12}$ClN$_5$O$_2$S.0.7 H$_2$O: % C, 30.21; % H, 4.85; % N, 25.16. Found: % C, 30.07; % H, 4.66; % N, 25.04.

$^1$H NMR (DMSO-d6) δ: 5.40–5.31 (m, 1H), 4.25 (dd, 1H), 3.43 (d, 1H), 3.13 (t, 1H), 2.69 (d, 1H), 2.38–2.15 (m, 3H).

EXAMPLE 10

2SR-4RS-4-(((1H-tetrazol-5-yl)thio)methyl) piperidine-2-carboxylic acid

A. Ethyl 2SR,4SR-4-(((4-nitrophenyl)sulfonyl)methyl)-N-(t-butoxycarbonyl)piperidine-2-carboxylate To a 0° C. solution of ethyl 2SR,4SR-4-hydroxymethyl-N-(t-butoxycarbonyl)piperidine-2-carboxylate (0.6 mmole, 0.17 g), triethylamine (0.6 mmole, 0.06 g), and DMAP (0.06 mmole, 0.007 g) in dichloromethane (1.5 mL) was added p-nitrobenzene sulfonyl chloride (0.6 mmole, 0.13 g) in dichloromethane (0.66 mL) and acetonitrile (0.33 mL). After 1 hr at 0° C. and 2 hours at room temperature, the reaction mixture was cooled to 0° C. and treated with triethylamine (0.3 mmole, 0.03 g) and then with p-nitrobenzene sulfonyl chloride (0.3 mmole, 0.6 g) in acetonitrile (0.5 mL). The mixture was stirred at room temperature for 1 hr, then treated with water (5 mL). The layers were separated and the organic layer washed with water (3×5 mL). The organic layer was dried (NaCl/MgSO$_4$), filtered and concentrated in vacuo to afford 0.21 g (75%) of the title compound.

Analysis calculated for C$_{20}$H$_{28}$N$_2$O$_9$S: % C, 50.84; % H, 5.97; % N, 5.93. Found: % C, 50.59; % H, 5.80; % N, 5.94.

Fast Atom Bombardment Mass Spectrum: M+1=473

B. Ethyl 2SR,4RS-4-(((1H-tetrazol-5-yl)thio)methyl)-N-(t-butoxycarbonyl)piperidine-2-carboxylate A solution of the compound from Example 10A (1.7 mmole, 0.78 g), 5-mercapto-1H-tetrazole (5.0 mmole, 0.51 g) and triethylamine (1.8 mmole, 0.18 g) in acetonitrile (11.5 mL) was stirred at 58° C. for 3.5 hr, heated to reflux for 4 hr then stirred at room temperature overnight. The mixture was filtered and the solids washed with acetonitrile (6 mL). The filtrate was concentrated in vacuo until a precipitate formed and the insolubles collected by filtration. The filtrate was concentrated in vacuo to afford a solid. This material was treated with ethyl acetate (5 mL) and water (5 mL), the pH of the biphasic solution adjusted from 2.8 to 8.2 with 1N sodium hydroxide (3.1 mL) and the layers separated. The aqueous layer was treated with ethyl acetate (5 mL), the pH adjusted from 7.9 to 2.4 with 1N hydrochloric acid (3.2 mL), then the layers separated and the organic layer dried (MgSO$_4$), filtered and concentrated in vacuo. The residue was subjected to reverse layer chromatography (C18 column packing) eluting with 50:49:1 acetonitrile:water:acetic acid to afford 0.19 g (30%) of the title compound.

Analysis calculated for C$_{15}$H$_{25}$N$_5$O$_4$S: % C, 48.50; % H, 6.78; % N, 18.85; % S, 8.63. Found: % C, 48.28; % H, 6.68; % N, 19.06; % S, 8.67.

Field Desorption Mass Spectrum: M+1=372.

C. A solution of the compound from Example 10B (0.3 mmole, 0.11 g) in 5N hydrochloric acid (25 mL) was heated to 45° C. for 16 hr, then heated to 71° C. for 2 hr. The mixture was cooled to room temperature and concentrated in vacuo. The residue was treated with water (2 mL), reduced in volume to about 1 mL, cooled to 0° C. for 30 min, and the crystals that formed were collected by filtration to afford 6 mg of the title compound. A second crop of crystals yielded 12 mg of the title compound. The title compound contains approximately 180 mol % of 5-mercapto-1H-tetrazole as an impurity.

Analysis calculated for C$_8$H$_{13}$N$_5$O$_2$S.1.8 C$_8$H$_2$N$_4$S: % C, 27.56; % H, 3.92; % N, 40.01. Found: % C, 27.68; % H, 3.93; % N, 40.60.

Field Desorption Mass Spectrum: M+1=244.

EXAMPLE 11

2SR,4SR-4-((5-mercapto-1H-tetrazol-1-yl)methyl)-piperidine-2-carboxylic acid

A. Ethyl 2SR,4SR-4-(((5-(2-oxo-2-phenylethyl)thio)-1H-tetrazol-1-yl)methyl)-N-(t-butoxycarbonyl)piperidine-2-carboxylate To a 0° C. solution of triphenylphosphine (0.18 mole, 48.4 g), ethyl 2SR,4SR-4-hydroxymethyl-N-(t-butoxycarbonyl)

piperidine-2-carboxylate (0.17 mole, 48.24 g) and 5-((2-oxo-2-phenylethyl)thio)-1H-tetrazole (0.18 mole, 40.67 g) in tetrahydrofuran (293 mL) and acetonitrile (293 mL) was added diethylazodicarboxylate (0.18 mole, 32.1 g). After addition was complete, the cooling bath was removed and the mixture was stirred at room temperature for 5 hr. The reaction was diluted with tetrahydrofuran (100 mL), stirred at room temperature for 24 hr, the insolubles collected by filtration and washed with 1/1 acetonitrile/tetrahydrofuran (50 mL). The filtrate was concentrated in vacuo, diluted with toluene (200 mL), filtered and the solid washed with toluene (25 mL). The filtrate was again concentrated in vacuo, the residue diluted with toluene (10 mL) and diethyl ether (200 mL), filtered and the filtrate concentrated in vacuo. The residue was dissolved in dichloromethane (500 mL) and washed with saturated aqueous sodium bicarbonate (3×100 mL). The organic layer was dried ($MgSO_4$), filtered and concentrated in vacuo. Flash silica gel filtration of the residue (hexane/diethyl ether gradient: 6/1, 3 L; 3/1, 2 L; 1/1, 3 L, and 0/100, 9.5 L) afford 5.1 g (6%) of the title compound.

Analysis calculated for $C_{23}H_{31}N_5O_5S$: % C, 56.42; % H, 6.38; % N, 14.30. Found: % C, 56.22; % H, 6.35; % N, 14.11.

Field Desorption Mass Spectrum: M+1=490.

B. Ethyl 2SR,4SR-4-((5-mercapto-1H-tetrazol-1-yl)methyl)-N-(t-butoxycarbonyl)piperidine-2-carboxylate A solution of the compound from Example 11A (3.6 mmole, 1.8 g) in ethanol (300 mL) was subjected to photolysis (450 W mercury arc lamp, pyrex filter) for 4 hr. The reaction mixture was concentrated in vacuo, treated with ethyl acetate and water, the pH adjusted from 3.0 to 8.3 with 1N sodium hydroxide, the layers separated and the organic layer washed with water (2×50 mL). The combined aqueous layers were treated with dichloromethane (250 mL), the pH adjusted from 8.6 to 2.5 with 1N hydrochloric acid, the layers separated and the aqueous layer extracted with dichloromethane (3×50 mL). The combined organic layers were dried ($MgSO_4$), filtered and concentrated in vacuo to afford 0.84 g (62%) of the title compound.

Analysis calculated for $C_{15}H_{25}N_5O_4S$: % C, 48.50; % H, 6.78; % N, 18.85. Found: % C, 48.78; % H, 6.90; % N, 19.02.

Field Desorption Mass Spectrum: M+1=372.

C. A solution of the compound from example 11B (6.5 mmole, 2.4 g) in ethanol (10 mL) was treated with 5N hydrochloric acid (200 mL). The mixture was heated and ethanol removed by distillation, then refluxed for 4.5 hours, cooled to room temperature and concentrated in vacuo. Cation exchange chromatography afforded a solid that was suspended in acetone (70 mL), refluxed for 50 minutes, cooled to room temperature, filtered and washed with acetone (40 mL) and diethyl ether (100 mL) to afford 1.4 g (89%) of the title compound.

Analysis calculated for $C_8H_{13}N_5O_2S$: % C, 35.43; % H, 5.98; % N, 25.82. Found: % C, 35.44; % H, 5.58; % N, 25.82.

Field Desorption Mass Spectrum: M+1=244.

EXAMPLE 12

2SR,4SR-4-((4-mercapto-2H-tetrazol-2-yl)methyl)-piperidine-2-carboxylic acid

A. Ethyl 2SR,4SR-4-((5-((2-oxo-2-phenylethyl)thio)-2H-tetrazol-2-yl)methyl)-N-(t-butoxycarbonyl)piperidine-2-carboxylate A solution of the compound from Example 10A (2.0 mmole, 0.95 g), 5-((2-oxo-2-phenylethyl)thio)-1H-tetrazole (4.0 mmole, 0.88 g) and triethylamine (4.0 mmole, 0.40 g) in dimethylforamide (5 mL) was stirred at room temperature for 2 hr, at 42° C. for 6 hr and at room temperature overnight. At this time the mixture was treated with 5-((2-oxo-2-phenylethyl))thio-1H-tetrazole (1.0 mmole, 0.22 g) and triethylamine (1.0 mmole, 0.10 g), then heated at 67° C. for 2 hr. The mixture was cooled to room temperature, concentrated in vacuo, treated with ethyl acetate (25 mL) and water (10 mL), the layers separated and the organic layer washed with water (3×5 mL). The organic layer was washed with saturated aqueous sodium bicarbonate (2×5 mL) and brine (5 mL), then dried ($MgSO_4$), filtered and concentrated in vacuo. The residue was treated with acetonitrile (3 mL) and cyclohexane (0.5 mL), the precipitate collected by filtration and washed with 9/1 acetonitrile/cyclohexane to afford 0.073 g (7%) of the title compound.

Analysis calculated for $C_8H_{13}N_5O_2S$: % C, 55.81; % H, 6.43; % N, 14.15. Found: % C, 55.85; % H, 6.43; % N, 13.85.

Field Desorption Mass Spectrum: M+1=490.

B. 2SR,4SR-4-((5-((2-oxo-2-phenylethyl)thio)-2H-tetrazol-2-yl)methyl)-piperidine-2-carboxylic acid A suspension of the compound from Example 12A (0.5 mmole, 0.23 g) and 1N sodium hydroxide (2 mL) in acetonitrile (3.5 mL) and tetrahydrofuran (1 mL) was stirred 4 hr at room temperature. The mixture was treated with 1N hydrochloric acid (5 mL) then concentrated in vacuo. The residue was treated with 5N hydrochloric acid and heated at 72° C. for 1.5 hr and at reflux for 1.5 hr, then stirred overnight at room temperature. The mixture was concentrated in vacuo to a small volume and the pH adjusted to 6.9 with 1N sodium hydroxide. Anion exchange chromatography afforded material that was dissolved in water and subjected to cation exchange chromatography, which afforded 0.11 g (65%) of the title compound, used without further purification.

Field Desorption Mass Spectrum: M+1=362.

C. A solution of the compound from Example 12B (0.26 mmole, 0.095 g) and zinc dust (0.53 mmole, 0.034 g) in formic acid (1.5 mL) was stirred at room temperature for 8 hr and at −10° C. for 24 hours then concentrated in vacuo. The residue was treated with water (4 mL) and diethyl ether (15 mL), the layers separated, and the organic layer washed with water (3×2 mL). The combined aqueous washes were diluted with methanol (35 mL), the resulting precipitate collected by filtration and washed with 17/1 methanol/water, then the filtrate concentrated in vacuo. The residue was treated with water (10 mL) and methanol (25 mL), diatomaceous earth was added, and the insolubles collected by filtration and washed with 2.5/1 methanol/water. The filtrate was concentrated in vacuo, the residue treated with water (10 mL) and methanol (25 mL), diatomaceous earth was added and the insolubles collected by filtration and washed with 8/1 methanol/water. All of the collected insolubles were combined, treated with 1N hydrochloric acid (25 mL) and refluxed for 1 hour. The suspension was filtered while hot and the filtrate concentrated in vacuo. Cation exchange chromatography of the residue afforded 0.06 g (64%) of the title compound.

Field Desorption Mass Spectrum: M+1=244.

$^1$H NMR (DMSO-d6) δ: 4.27 (m, 2H), 3.70–3.66 (m, 1H), 3.20–3.13 (m, 1H), 2.86–2.75 (m, 1H), 2.22–2.10 (m, 1H), 1.99–1.83 (m, 1H), 1.64–1.56 (m, 1H), 1.37–1.19 (m, 2H).

These preparations are merely included as illustrative of the process of synthesizing some of the compounds of the invention. Similar processes can be used to synthesize similar compounds, as stated previously, and these processes are within the purview of those skilled in the art.

As noted above, the compounds of this invention are excitatory amino acid antagonists, more specifically, selective antagonists of the NMDA receptor. Therefore, another embodiment of the present invention is a method of blocking one or more NMDA excitatory amino acid receptors in mammals which comprises administering to a mammal preferably a human requiring decreased NMDA excitatory amino acid neurotransmission a pharmaceutically effective amount of a compound of the invention.

The term "pharmaceutically effective amount", as used herein, represents an amount of a compound of the invention which is capable of blocking one or more excitatory amino acid receptors. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. A typical daily dose will contain from about 0.01 mg/kg to about 20 mg/kg of the active compound of this invention. Preferred daily doses will be about 0.05 to about 10 mg/kg, ideally about 0.1 to about 5 mg/kg.

A variety of physiologic functions have been shown to be subject to influence by excessive stimulation of excitatory amino acid neurotransmission. As such, the compounds of the present invention are believed to have the ability to treat a variety of disorders in mammals associated with this condition which include neurological disorders such as convulsive disorders for example, epilepsy; stroke; anxiety; cerebral ischemia; muscular spasms; and neurodegenerative disorders such as Alzheimer's Disease and Huntington's Disease. Therefore, the present invention also provides methods of treating the above disorders at rates set forth above for excitatory amino acid receptors in mammals.

Experiments were performed to determine the effectiveness of the compounds of this invention as selective antagonists of the NMDA receptor subtype of excitatory amino acid receptors. The formula I compounds were tested for their ability to inhibit NMDA, AMPA, and kainic acid receptor binding to rat membranes in a radioligand binding assay using [$^3$H]CGS19755, [$^3$H]AMPA, and [$^3$H]KA.

For all radioligand binding assays, male Sprague-Dawley rats were used. Displacement of the specific binding [3H] CGS19755 (10 nM) to Triton-X-treated synaptosomal membranes of rat forebrain was used to determine NMDA receptor affinity. Non-specific binding was determined using 10 mM L-glutamate. Samples were incubated in an ice-bath for 30 minutes, and bound ligand was separated from the free ligand by rapid filtration through WHATMAN GF/B glass fiber filters. Murphy, et al., *British J. Pharmacol.*, 95, 932–938 (1988). Kainate binding was performed using washed synaptosomal membranes from the rat forebrain as described by Simon, et al. Simon, et al., *J. Neurochem.*, 26, 141–147 (1976). Tritiated kainate (5 nM) was added to 50 mM Tris-HCl buffer (pH 7.4 at 4° C.) containing 200–300 mg/ml of tissue protein. Samples were incubated for 30 minutes in an ice-bath, then rapidly filtered using a Brandel cell harvester and WHATMAN GF/C filters. Filters were washed twice with 3 ml of cold buffer. Non-specific binding was determined using 100 mM non-labeled kainate. The binding of [$^3$H]AMPA (5 nM) was conducted with crude membranes of rat forebrain in the presence of 100 mM KSCN as described by Nielson, et al. Nielson, et al., *Eur. J. Med. Chem. Chim. Ther.*, 21, 433–437 (1986). Non-specific binding was determined with 10 mM non-labeled AMPA.

The concentration of the formula I compound that inhibited 50% binding (IC$_{50}$, mean±standard error, n=3) as calculated by linear regression of displacement data transformed to the Hill equation as described by Bennett. Bennett, Neurotransmitter Receptor Binding, 57–90 (1978).

Compounds of the instant invention tested in the above assays were found to act as NMDA receptor ligands at concentrations less than 20 μM. The same compounds exhibited poor affinity at the AMPA and KA receptors.

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

In general, the compounds of the invention are most desirably administered at a concentration that will generally afford effective results without causing any harmful or deleterious side effects and can be administered either as a single unit dose, or if desired, the dosage may be divided into convenient subunits administered as suitable times throughout the day.

The compositions are preferably formulated in a unit dosage form, each dosage containing from about 0.10 to about 500 mg, more usually about 1 to about 100 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier. However, it will be understood that the amount of the compound actually administered will be determined by a physician, in the light of the relevant circumstances including the choice of compound to be administered, the chosen route of administration, the age, weight, and response of the individual patient, and the severity of the patient's symptoms, and therefore the above dosage ranges are not intended to limit the scope of the invention in any way.

The following formulation examples are illustrative only and are not intended to limit the scope of the invention in any way.

Formulation 1

Hard gelatin capsules are prepared using the following ingredients:

|  | Quantity (mg/capsule) |
| --- | --- |
| 2SR,4RS-4-( ( (1H-Tetrazol-5-yl)methyl)oxy) piperidine-2-carboxylic acid | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/capsule) |
| --- | --- |
| 2SR,4RS-4-( ( ( (1H-Tetrazol-5-yl)methyl)oxy) methyl)piperidine-2-carboxylic acid | 250 |
| cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
| --- | --- |
| E and Z 2SR-4-(O-(1H-Tetrazol-5-yl)methyl)ketoximino)piperidine-2-carboxylic acid | 0.25 |
| ethanol | 29.75 |
| Propellant 22 (chlorodifluoromethane) | 70.00 |
| Total | 100.00 mg |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

|  | Quantity (mg/capsule) |
| --- | --- |
| 2SR,4SR-4-( (1H-Tetrazol-5-yl)thio)piperidine-2-carboxylic acid | 60 |
| starch | 45 |
| microcrystalline cellulose | 35 |
| polyvinylpyrrolidone (as 10% solution in water) | 4 |
| sodium carboxymethyl starch | 4.5 |
| magnesium stearate | 0.5 |
| talc | 1 |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. Sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

|  | Quantity (mg/capsule) |
| --- | --- |
| 2SR,4RS-4-( (1H-Tetrazol-5-yl)thio)piperidine-2-carboxylic acid | 80 |
| starch | 59 |
| microcrystalline cellulose | 59 |
| magnesium stearate | 2 |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient may be made as follows:

|  | Quantity (mg/capsule) |
| --- | --- |
| 2SR,4RS-4-( (5-mercapto-1H-Tetrazol-1-yl)piperidine-2-carboxylic acid | 225 |
| saturated fatty acid glycerides | 2,000 |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| | Quantity (mg/capsule) |
|---|---|
| 2SR,4RS-4-(5-mercapto-2H-Tetrazol-2-yl)piperidine-2-carboxylic acid | 50 |
| sodium carboxymethyl cellulose | 50 |
| syrup | 1.25 |
| benzoic acid solution | 0.10 |
| flavor | q.v. |
| color | q.v. |
| Purified water total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | Quantity (mg/capsule) |
|---|---|
| 2SR,4RS-4-(S-mercapto-1H-Tetrazol-5-yl)piperidine-2-carboxylic acid | 100 |
| isotonic saline | 1000 |
| Total | |

The solution of the above ingredients is administered intravenously at a rate of 1 ml per minute to a subject in need of treatment.

We claim:

1. A compound of the general formula:

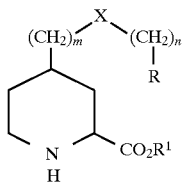

wherein:

X is =NO—, —O—, —S— or —(CH$_2$)$_q$—;
m, n and q are 0 or 1;
R is

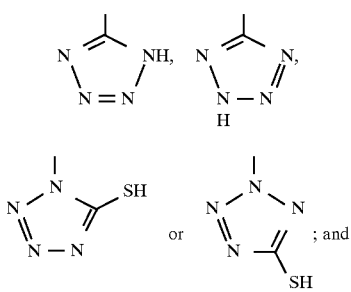

R$^1$ is H or a carboxyl protecting group;
or a pharmaceutically acceptable salt, racemate or isomer thereof, provided that;
when X is —O—, n must be 1;
when X is —O—, —S— or =NO—, R must be

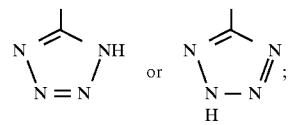

when X is =NO—, m must be 0;
and when X is (CH$_2$)$_q$, R must be

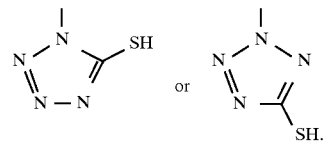

2. The compound of claim 1 wherein m is 0, n is 1 and X is oxygen.
3. The compound of claim 1 where m is 0, n is 0 and X is S.
4. The compound of claim 1 that is 2SR,4RS-4-(((1H-Tetrazol-5-yl)methyl)oxy)piperidine-2-carboxylic acid; 2SR,4RS-4-((((1H-Tetrazol-5-yl)methyl)oxy)methyl) piperidine-2-carboxylic acid; E and Z 2SR-4-(O-(1H-Tetrazol-5-yl)methyl)ketoximino)piperidine-2-carboxylic acid; 2SR,4RS-4-((1H-Tetrazol-5-yl)thio)piperidine-2-carboxylic acid; 2SR,4RS-4-((1H-Tetrazol-5-yl)thio) piperidine-2-carboxylic acid; 2SR,4RS-4-(5-mercapto-1H-Tetrazol-1-yl)piperidine-2-carboxylic acid; 2SR,4RS-4-(5-mercapto-2H-Tetrazol-2-yl)piperidine-2-carboxylic acid; 2SR,4RS-4-(5-mercapto-1H-Tetrazol-1-yl)piperidine-2-carboxylic acid; 2SR,4RS-4-(5-mercapto-2H-Tetrazol-2-yl) piperidine-2-carboxylic acid; 2SR,4RS-4-(((1H-Tetrazol-5-yl)thio)methyl)piperidine-2-carboxylic acid; 2SR,4RS-4-( (5-mercapto-1H-Tetrazol-1-yl)methyl)piperidine-2-carboxylic acid; or 2SR,4RS-4-((5-mercapto-2H-Tetrazol-2-yl)methyl)piperidine-2-carboxylic acid.
5. A method of blocking one or more excitatory amino acid receptors in mammals which comprises administering to a mammal requiring decreased excitatory amino acid neuro-transmission a NMDA receptor antagonistic effective amount of a compound of claim 1.
6. A method of treating epilepsy in mammals comprising administering to a mammal in need of treatment for epilepsy an antiepileptic amount of a compound of claim 1.
7. A method of treating stroke in mammals comprising administering to a mammal in need of treatment for stroke an antistroke amount of a compound of claim 1.
8. A method of treating anxiety in mammals comprising administering to a mammal in need of treatment for anxiety an antianxiety amount of a compound of claim 1.
9. A method of treating cerebral ischemia in mammals comprising administering to a mammal in need of treatment for cerebral ischemia an antiischemic amount of a compound of claim 1.
10. A method of treating muscle spasms in mammals comprising administering to a mammal in need of treatment for muscle spasms an antispasmodic amount of a compound of claim 1.
11. A method of claim 5 wherein the mammal is a human.
12. A pharmaceutical formulation comprising a NMDA receptor antagonistic effective amount of a compound of claim 1 and a pharmaceutically acceptable carrier, diluent, or excipient therefor.

* * * * *